United States Patent [19]

Edelman et al.

[11] Patent Number: 5,100,668

[45] Date of Patent: Mar. 31, 1992

[54] CONTROLLED RELEASE SYSTEMS CONTAINING HEPARIN AND GROWTH FACTORS

[75] Inventors: Elazer R. Edelman, Brookline; Robert S. Langer, Somerville; Michael Klagsburn, Newton; Edith Mathiowitz, Brookline, all of Mass.

[73] Assignee: Massachusetts Institute of Technology, Cambridge, Mass.

[21] Appl. No.: 206,520

[22] Filed: Jun. 14, 1988

[51] Int. Cl.⁵ .................... A61F 13/00; A61F 2/00; A61K 9/14

[52] U.S. Cl. .................... 424/422; 424/423; 424/426; 424/484; 424/485; 424/488; 530/399; 530/813; 530/815; 530/816; 536/51

[58] Field of Search ............ 435/178, 179, 180, 182; 424/426, 422, 488, 484, 485; 530/813, 815, 816, 399; 536/51

[56] References Cited

U.S. PATENT DOCUMENTS

| | | | |
|---|---|---|---|
| 3,645,852 | 2/1972 | Axen et al. | 530/816 X |
| 3,647,630 | 3/1972 | Franks | 435/179 |
| 3,730,841 | 5/1973 | Salvatore et al. | 435/182 |
| 3,746,621 | 7/1973 | Kondo et al. | 435/179 X |
| 4,038,140 | 7/1977 | Jaworek et al. | 435/178 |
| 4,070,348 | 1/1978 | Kraemer | 525/54.2 X |
| 4,137,127 | 1/1979 | Stocker | 435/178 X |
| 4,138,292 | 2/1979 | Chibata et al. | 435/178 X |
| 4,164,560 | 8/1979 | Folkman et al. | 435/182 X |
| 4,373,023 | 2/1983 | Langer et al. | 435/178 X |
| 4,407,957 | 10/1983 | Lim | 435/178 |
| 4,464,468 | 8/1984 | Avrameas et al. | 435/182 X |
| 4,613,665 | 9/1986 | Larm | 525/54.2 X |
| 4,678,671 | 7/1987 | Feijen et al. | 424/484 |
| 4,786,501 | 11/1988 | Janski et al. | 424/426 X |

FOREIGN PATENT DOCUMENTS

0086186 7/1983 European Pat. Off.

OTHER PUBLICATIONS

Murphy et al., *Molecular Endocrinology*, 2(7) (1988).
Zhou et al., *J. of Chromatograpy*, 476 (1989).
Walicke et al., *Proc. Natl Acad. Sci. U.S.A.*, 83:3012-3016 (1986).
Folkman et al., *Science*, 235:442 (1987).
Sullivan et al., *J. Tissue Culture Meth.*, 10(2):125 (1986).
Langer et al., *Methods in Enzymology*, 112:399 (1985).
Murray et al., *Cancer Drug Delivery*, 1(2):119 (1984).
Murray et al., *In Vitro*, 19(10):743 (1983).
Langer et al., *Annal. N. Y. Acad. Sci.*, (reprint), 1.

Primary Examiner—Thurman K. Page
Assistant Examiner—G. S. Kishore
Attorney, Agent, or Firm—Hamilton, Brook, Smith & Reynolds

[57] ABSTRACT

A system for stabilizing fibroblast-derived growth factors, maintaining their bioactivity over a prolonged period of time and controllably releasing them for use is disclosed. The system uses growth factors bound to biocompatible substrates via heparin or heparin derived compounds to maintain the bioactivity of the growth factors. A growth factor bound to a heparin coated substrate can be used independently as a controlled release device, or can be incorporated into a reservoir or matrix type controlled release devices to further enhance the controlled release properties. The stabilized growth factors can be implanted into a patient, thereby providing a means for producing an in vivo controlled release of a growth factor to the patient.

10 Claims, 2 Drawing Sheets

CONTROLLED RELEASE SYSTEMS CONTAINING HEPARIN AND GROWTH FACTORS

GOVERNMENT SUPPORT

The government may have rights in this invention as it was sponsored in part by Grant No. 26698 of the National Institutes of Health.

BACKGROUND OF THE INVENTION

It has become apparent that blood-borne and blood vessel bound factors play a major role in the propagation and persistence of a large number of diseases in many different fields of medicine. The growth of tumors, progression of arthritis, and propagation of atherosclerosis are but a few of the important clinical scenarios in which growth factor (GF) control has been demonstrated.

This control is presumed to stem from the basic dependence of these diseases, and others like them, on blood vessels for nourishment and support. The growth and replication of the endothelial cells that line the blood vessels and the smooth muscle cells that surround the blood vessels appears to be modulated by an expanding family of GFs. The growth factors that stimulate endothelial cells have a strong affinity for heparin. As such, the effects of heparin and heparin avid growth factors and their inhibitors are the subject of extensive study.

While heparin avid growth factors are highly potent, they tend to degrade rapidly and are currently in short supply. Thus, they cannot be ingested or injected and in vivo studies, if possible at all, are limited to only the most short term effects of minute quantities of factor.

The technology of controlled drug delivery provides an effective means of storing and delivering a wide variety of pharmaceuticals. Unfortunately, the development of a controlled release growth factor system has been hindered by a number of significant problems. Key among these are denaturation and loss of biological activity when such factors are stored for prolonged periods, as well as enhanced loss when exposed to the procedures of standard controlled release device (CRD) fabrication. For example, even if stored in the most concentrated formulations at optimum temperatures, over 90% of the biological activity of many growth factors is lost in four weeks.

In addition, conventional means of CRD encapsulation press or dissolve an encapsulating material around the pharmaceutical. This generally requires exposing a mixture of the pharmaceutical and the encapsulating material to an elevated temperature, pressure or ionic strength. Extremes of pH or contact with organic solvents might also be required. Each of these exposures is known to drastically denature growth factors.

Additionally, simply encapsulating microliter quantities of growth factors has proven problematic. It is exceedingly difficult to obtain uniform dispersion of such a small quantity of liquid within any of the conventional controlled release devices. Attempts to overcome this drawback by dilution with other liquids or lyophilization of the growth factors in combination with other powdered materials have enhanced the loss of biological activity.

Thus, a need exists for a method for preventing the denaturation and loss of bioactivity of growth factors when stored for prolonged periods. Additionally, a need exists for a controlled release device compatible with growth factors that would allow them to be released at a generally uniform, or at least predictable, rate over a period of time.

SUMMARY OF THE INVENTION

This invention pertains to a device for stabilizing heparin bound growth factors and controlling their release rate. More specifically, this invention pertains to a device wherein growth factors which bind to heparin and heparin-derived substances are stabilized by forming a complex between a growth factor and heparin or heparin-derived substances and binding the complex to a biocompatible substrate. The biological activity of growth factors contained in this heparin/growth factor complex has been found to be significantly maintained over prolonged time periods, especially when compared to unbound growth factor samples.

The stabilized growth factors of this invention exhibit a controlled release from heparin-bound substrate surfaces. This controlled release can be further enhanced by incorporating the growth factor/heparin/substrate unit into a conventional controlled release device. Satisfactory results have been demonstrated using the two basic types of CRDs, reservoir-type and matrix-type controlled release devices. Both types of controlled release devices are suitable for implantation and in vivo release of growth factors.

The advantages of this invention include the ability to store growth factors for prolonged periods while maintaining a significant amount of biological activity, and the ability to incorporate growth factors into devices for controllable release over extended periods without destroying biological activity. The devices of this invention are simple to produce, easy to store and use, and inexpensive when compared to the cost of the growth factor itself.

DETAILED DESCRIPTION OF THE INVENTION

Figure 1:
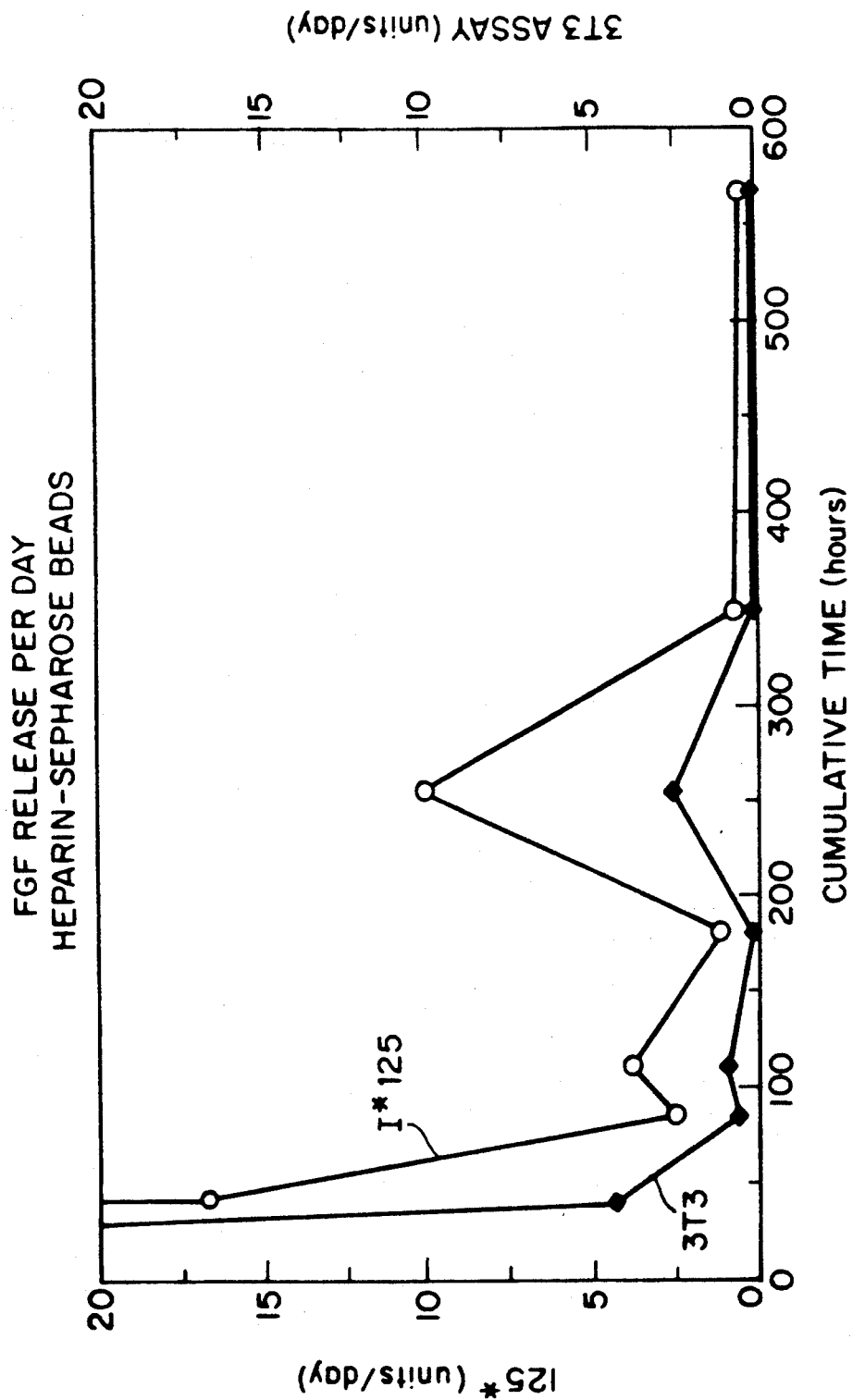
FIG. 1 is a plot of the release rate and bioactivity over time for fibroblast-derived growth factor (FGF) bound to heparin-coated dextran beads.

The methods described herein have been found to work successfully with fibroblast derived growth factor (FGF) because of its heparin affinity.

Fibroblast derived growth factors (both acidic and basic) are 154-amino acid polypeptides blocked at the amino terminus. They are believed to play a major role in angiogenesis, response to injury and tissue repair. A more detailed discussion of various FGFs and related growth factors is presented by Folkman and Klagsbrun in Science, 235, 442 (1987), the teachings of which are incorporated herein by reference.

The fibroblast derived growth factors also include truncated forms produced by proteinase cleavages at the amino terminal ends. These truncated forms include basic FGF, a 146-amino polypeptide (Folkman et al., Science Vol. 235, p. 442–447 (1987); F. Esch et al., Proc. Natl. Acad. Sci. USA 82:6507 (1985) and acidic FGF, a 140-amino acid polypeptide (Folkman et al, cited supra; K. A. Thomas et al Proc. Natl. Acad. Sci. USA 82: 6409

(1985); G. Gimencz-Gallego et al., Science 230:1385 (1985); F. Esch et al., Biochem. Biophys. Res. Commun. 133:544 (1985). Basic and acidic FGF are structurally related having 53% sequence homology. There are two classes of endothelial cell growth factors whose protypes are acidic and basic FGF (Schreiber et al., J. Cell Biol. 101:1623 (1985); Lobb et al., J. Biol. Chem. 261:1924 (1986)). The growth factors in a class are either identical or represent multiple molecular weight forms of the same polypeptide.

One class of heparin-binding endothelial cell growth factors (hereinafter ECGF's) consists of anionic polypeptides that elute from heparin-Sepharose columns with approximately 1.0M NaCl. They have isoelectric points of 5 to 7 and molecular weights of 15,000 to 18,000. This class of heparin-binding growth factors has been found mainly in neural tissue and includes brain-derived acidic FGF (R. R. Lobb and J. W. Fett, Biochemistry 23:6295 (1984); K. A. Thomas et al., Proc. Natl. Acad. Sci. 81:357 (1984); and G. Conn and V. B. Hatcher, Biochem. Biophys. Res. Commun. 124:262 (1984)), ECGF (T. Maciag et al., Science 225:932 (1984)), eye-derived growth factor II (J. Courty et al., Biochemie 67:265 (1985)), and an acidic retina-derived growth factor (P. A. D'Amore and M. Klagsburn, J. Cell Biol. 99:1545 (1984)). The other class of heparin-binding endothelial cell mitogens consists of cationic polypeptides that elute from heparin-Sepharose with 1.5M NaCl. These polypeptides have isoelectric points of 8 to 10, molecular weights between 16,000 and 18,500, and appear to be identical to basic FGF or multiple molecular weight forms of it. The cationic class of heparin-binding growth factor appears to be more ubiquitous than the anionic. Polypeptides of the basic FGF class have been isolated from sources such as pituitary (F. Esch et al., Proc. Natl. Acad. Sci. USA 82:6507 (1985), brain (R. R. Lobb and J. W. Fett, Biochemistry 23:6295 (1984); D. Gospodarowicz et al., Proc. Natl. Acad. Sci. USA 81:6963 (1984); and P. Bohlen et al., Proc. Natl. Acad. Sci. USA 81:5364 (1984)), hypothalamus (M. Klagsburn and Y. Shing Proc. Natl. Acad. Sci. USA 82:805 (1985)), eye (J. Courtney et al., Biochimie 67:265 (1985)), cartilage (R. Sullivan and M. Klagsburn, J. Biol. Chem. 260:2399 (1985)), bone (P. V. Hauschka et al., J. Bio. Chem. 61:12665 (1986)), corpus luteum (D. Gospodarowicz et al., Endocrinology 117:2283 (1985)), adrenal gland (D. Gospodarowicz et al., Endocrinology 118:82 (1986)), kidney (A. Baird et al., Regular. Peptides 12:201 (1985)), placenta (D. Moscatelli et al., Proc. Natl. Acad. Sci. USA 83:2091 (1986)), macrophages (A. Baird et al., Biochem. Biophys. Res. Commun. 126:358 (1985)), chondrosarcoma (Y. Shing et al., Science 223:1296 (1984)), and hepatoma cells (M. Klagsburn et al., Proc. Natl. Acad. Sci. USA 83:2448 (1986)).

A human cDNA clone encoding ECGF, a precursor of acidic FGF, was isolated from a library of human brain stem cDNA (M. Jaye et al., Science 233:541 (1986)) and a bovine cDNA clone encoding basic FGF has been isolated from a pituitary cDNA library (J. A. Abraham et al., Science 233:545 (1986)). The size of the human ECGF messenger RNA (mRNA) transcript is 4.8 kg; whereas 5-kb and 2.2-kb mRNA transcripts for basic FGF have been identified. In both genes the predicted amino acid sequences of the open reading frame begin with methionine start codon followed by 154 amino acids. Amino acid sequence analysis of ECGF (W. H. Burgess et al., Proc. Natl. Acad. Sci. USA 83:7216 (1986)) and basic FGF (N. Ueno et al., Biochem Biophys. Res. Commun. 138:580 (1986)) is in agreement with the gene sequence data and indicates that both are 154-amino acid polypeptides blocked at the amino terminus. It is now apparent that the lower molecular weight forms of acidic and basic FGF that were originally isolated and sequenced were truncated forms produced by proteinase cleavages at the amino-terminal end (W. H. Burgess et al., Proc. Natl. Acad. Sci. USA 83:7216 (1986); N. Ueno et al., Biochem. Biophys. Res. Commun. 138:580 (1986); W. H. Burgess et al., J. Biol. Chem. 260:11389 (1985); and M. Klagsburn et al., Proc. Natl. Acad. Sci. USA in press). These include the 140-amino acid form of acidic FGF (K. A. Thomas et al., Proc. Natl. Acad. Sci. USA 82:6409 (1985); G. Gimenez-Gallego et al., Science 230:1385 (1985); and F. Esch et al., Biochem. Biophys. Res. Commun. 122:554 (1985)) and the 146-amino acid forms of basic FGF (D. Gospodarowicz et al., Proc. Natl. Acad. Sci. USA 81:6963 (1984); and F. Esch et al., Proc. Natl. Acad. Sci. USA 82:6507 (1985)). Unfortunately, as stated previously, FGF tends to denature and lose activity when stored for prolonged periods of time, especially at elevated temperatures.

Heparin is a heterogenous group of straight-chain anionic mucopolysaccharides, called glycosaminoglycans, of molecular weights that average 15,000 daltons. Commercial heparin comprises polymers of two repeating disaccharide units; D-glucosamine-L-iduronic acid and D-glucosamine-D-glucuronic acid. Heparin is strongly acidic because it has a high content of covalently linked sulfate and carboxylic acid groups.

Related to heparin, and therefore also useful with this invention are substances such as heparan sulfate. As used herein, however, unless specifically distinguished, the term heparin is intended to apply to both heparin and heparin-derived compounds such as heparan sulfate.

Heparin and heparin-derived compounds have been found to stabilize many of the storage losses of FGF, especially those resulting from elevated temperatures. Furthermore, the stabilizing effect of heparin and derived substances has been combined with its ability to bind FGF. This binding ability allows the formation of a stable growth factor carrier in a solid form.

More specifically, heparin can bind to the surfaces of a wide variety of materials by enzymatic linking. Thus, growth factors that can bind to heparin, such as the FGFs, can then be made to stick to the surface of these materials, thereby allowing the use of a variety of sustained release devices using growth factors.

A variety of controlled release devices can be produced which utilize the induced stability of growth factors when bound to heparin. The two basic CRDs are reservoir and matrix systems. In a reservoir CRD, the material to be released is housed within a porous envelope. The envelope surrounds a central core or reservoir of solid, liquid or gas which contains the material to be released. The core material must be able to diffuse through the envelope material and the rate of release depends upon the rate of diffusion as well as the porosity and tortuosity of pores within the envelope. Large molecular compounds, therefore, are poorly and erratically released from these systems.

Controlled release of large molecular compounds can be achieved by using a matrix type CRD. In this system, the substance to be released is incorporated within the wall of the device. The word "matrix" refers to the homogeneous dispersion of drug through the wall of supporting material. The substance to be released is mixed as a dry powder with the supporting material. The mixture is then fabricated into a single monolithic device. The powder creates "caves" or channels within the device whose supporting walls are made up of the second material. If the molecular weight of the substance is large enough, it will not diffuse through the walls; rather, it must pass through the tortuous network of connecting channels to be released. The rate of release is dependent upon the ability of the environmental fluid to enter the matrix, solubilize the substance or drug, and leach the solubilized substance out of the matrix. The leaching time is determined not only by the net diffusitivities of the substance and its solvent, but also by the porosity, tortuosity and hydrophilicity of the matrix and the size and concentration of the substance embedded within the device.

Both reservoir-type and matrix-type CRDs can be produced from biocompatible materials. Use of such materials allows the device to be implanted into a patient, thereby providing an in vivo controlled release of growth factor to the patient.

Regardless of whether a reservoir or matrix CRD is to be used, it is first necessary to provide a heparin/growth factor complex bound to an immobilizing substrate. One suitable variety of substrates is the family of crosslinked dextran beads. As used herein, the term beads refers to small, discrete particles upon which a substance can be bound. Often, although not always, the beads useful in this invention are porous and are formed from polymers. A preferred bead substrate comprises diethylaminoethyl (DEAE)-substituted dextran beads. These beads are commercially produced by Pharmacia Fine Chemicals, Inc., Piscataway, NJ, under the tradename DEAE-Sephadex A50, an ion exchange system. Chemically, these beads are formed from a crosslinked dextran matrix having diethylaminoethyl groups covalently bound to the dextran chain. As commercially available, DEAE-Sephadex A50 beads are believed to have a particle size of 40–120 $\mu$m and a positive charge capacity of about 5.4 meq per gram of dry, crosslinked dextran (ignores weight of attached DEAE moieties). Other anion exchange resins, such as DEAE-Sephadex A25, QAE-Sephadex A50 and QAE-Sephadex A25 are suitable. Uncharged crosslinked dextran beads sold by Pharmacia under various Sephadex and Sepharose tradenames are also suitable for use with this invention.

In a preferred embodiment of the invention, the growth factor is bound to heparin after the heparin is bound to a substrate such as the previously described dextran beads. Crosslinked dextran beads having bound heparin are available commercially, or alternatively, can be produced by using cyanogen bromide to activate the surface of the beads, thereby allowing the surface to accept heparin. If growth factor is then passed over the beads, it sticks to the heparin which is bound to the bead surface. Tests using radiolabelled growth factor have demonstrated that over 80% of the growth factor passed over heparin-coated beads becomes bound to heparin.

Heparin-bound growth factor leaches off the beads at a steady and sustained rate. If desired, however, the growth factor can be almost entirely stripped from the beads by exposing them to high salt concentrations such as 3.0M NaCl.

The rate of growth factor released from the heparin-coated beads has been studied both radioactively and bioactively. The radioactive data relates to the physical presence of growth factor, while the bioactive data relates to the biological activity of the material which is being released. A composite graph of both radioactive data and bioactive data is presented in FIG. 1.

FIG. 1 represents the rate of FGF release from heparin-sepharose beads. The radioactive data was compiled using FGF radiolabelled with iodine-125, ($^{125}$I), designated in the Figure as I*125. The bioactive data was compiled using a 3T3 assay and is designated in the Figure as 3T3. The 3T3 assay is described in detail by Sullivan and Klagsburn in *J. Tissue Culture Meth.*, 10(2), 125 (1986), the teachings of which are incorporated herein by reference. FIG. 1 shows that the rate of FGF release from the bead surface is about 5–7% per day which corresponds to a release rate of approximately 2 units per day for this dose formulation. About 25% of the physically detected growth factor was found to have remained biologically active.

The above data confirms that growth factor can be bound to heparin coated dextran beads and be used in the fabrication of controlled release devices. The growth factor which might otherwise lose most of its activity with handling or encapsulation can be easily transported and enveloped after binding with heparin. The continuous, slow leaching of growth factor from the beads constantly replenishes the source of growth factor to be released from a CRD. These beads can be encapsulated within a controlled release device which stores the factor in the most biologically conservative form and provides for efficient encapsulation as well as an enhanced controlled release characteristic.

Many different methods, such as hot melt or solvent casting, for example, can be used to encapsulate heparin-bound growth factors. As a preferred embodiment of a reservoir system, however, heparin-bound growth factor is encapsulated in microspheres of sodium alginate. In this method, a sodium alginate solution is mixed with a measured quantity of heparin-dextran beads containing bound growth factor. This suspension is dropped into a hardening solution of calcium chloride. Spheres are formed as drops of the suspension enter the hardening solution. The utimate size of the microspheres can be controlled by controlling the diameter of the orifice through which suspension droplets are formed. The porosity of the sodium alginate envelope is determined by the degree of crosslinking of the alginate. The degree of crosslinking is dependent upon the residence time of the spheres in the calcium chloride bath. The greater the residence time, the harder the sodium alginate wall becomes.

Figure 2:
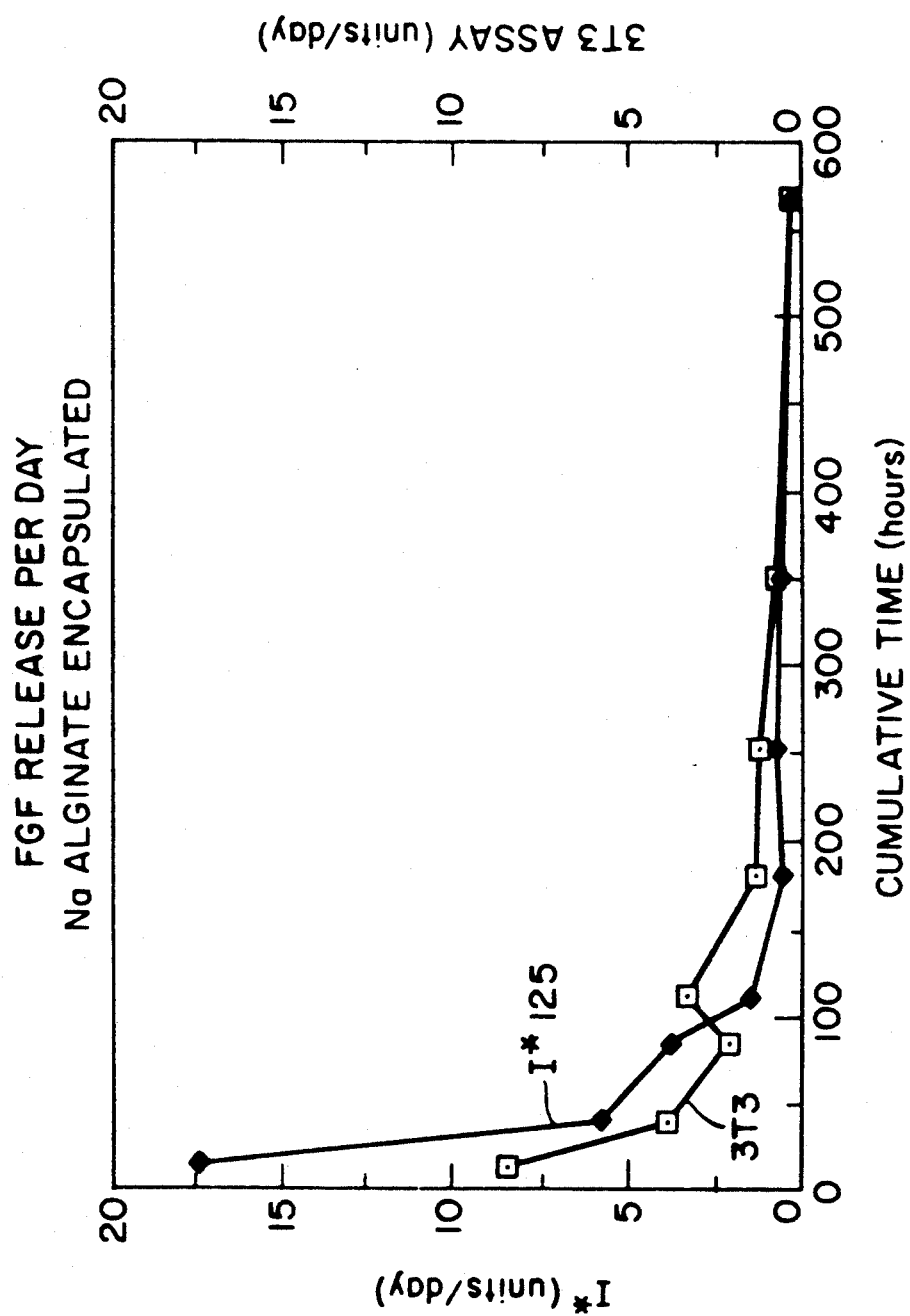
FIG. 2 is a plot of the release rate and bioactivity over time for a heparin-bound FGF suspended in a sodium alginate capsule.

FIG. 2 is a release profile of FGF from sodium alginate capsules for capsules allowed to harden for five minutes. As in FIG. 1, radio-labelled growth factor was used, and physical release was contrasted with biological activity. As demonstrated in FIG. 2, a slow, steady stream of growth factor was released through the wall of the device at approximately 1 unit per day.

The stream depicted in FIG. 2 represents growth factor which has leached off the heparin-dextran beads and diffused through the calcium-hardened, sodium alginate envelope. FIG. 2 also represents the bioactivity of the released FGF, showing that about 85% of the factor detected by $^{125}$I gamma counting can be detected by the 3T3 cell synthesis assay.

In contrast to FGF release profiles detected from similar beads not encapsulated, the bulk of what was released was released biologically intact. A number of possible explanations for this exist including the polymerization of inactivated forms within the microcapsule such that they are not released, and the retention of biological activity in the protected environment of the microcapsule.

The heparin-dextran beads containing bound growth factor can also be incorporated into a matrix-type CRD. While numerous methods for forming matrix CRDs are available, few are suitable for use with growth factors. In the preferred embodiment, FGF laden heparin-dextran beads are incorporated within the matrix using compression molding. In this method, a biologically inert polymeric material, such as the preferred ethylene-vinyl acetate copolymer (EVAc) is ground into fine particles. The substance to be embedded, in this case the growth factor laden beads, is mixed with the particulate polymeric material. This mixture is then placed in a compression chamber and compressed on a high pressure press to cause the two substances to meld together into a single structure. This device can then be implanted into a patient to provide a sustained release of the growth factor.

The beads of this invention have been mixed with EVAc and compressed. The resulting fabricated device had a generally supporting network of EVAc with interconnecting channels which housed the growth factor laden heparin-dextran beads.

Although the devices described in detail herein have been sodium alginate capsules and EVAc matrices, the invention is not intended to be limited to these embodiments. Any number of nonerodable, synthetic biocompatible materials can be used in the devices described herein. Additionally, bioerodable polymers such as polyanhydrides, polylactic acids, polyglycolic acids and copolymers thereof can be used in the practice of this invention.

Crosslinked dextran beads have been used as a substrate for the devices described herein, however, practically any biocompatible surface can be used as a substrate for heparin. Furthermore, a bead geometry was chosen for its large surface area; however, the substrate can be of any size or shape suitable for in vivo use.

Equivalents

Those skilled in the art will recognize, or be able to ascertain applying no more than routine experimentation, many equivalents to the specific embodiments described above. Such equivalents are intended to be encompassed within the following claims.

We claim:

1. A device for controlling the release rate of a fibroblast cross-linked dextran derived growth factor which comprises a substrate material having heparin or heparin sulfate bound thereto and the growth factor bound to the heparin or heparin sulfate.

2. A device as in claim 1 wherein the substrate of cross-linked dextran material comprises beads.

3. A device as in claim 1 wherein said device further comprises an encapsulation means.

4. A device as in claim 3 wherein the encapsulation means comprises a sodium alginate envelope.

5. A device as in claim 1 wherein said device is contained within a polymeric matrix.

6. A device as in claim 5 wherein the matrix comprises ethylene-vinyl acetate copolymer.

7. A device as in claim 6 wherein said device system is contained within a bioerodable polymer.

8. A device as in claim 7 wherein the bioerodable polymer is selected from the group consisting of polyanhydrides, polyactic acids, polyglycolic acids and copolymers thereof.

9. A reservoir sustained release device for the sustained release of fibroblast-derived growth factors which comprises:
   a. a biocompatible substrate of cross-linked dextran beads having heparin or heparin sulfate bound thereto and the growth factor bound to the heparin or heparin-sulfate;
   b. a sodium alginate solution surrounding the growth-factor-bound substrate; and
   c. a hardened sodium alginate envelope surrounding the solution and growth-factor-bound substrate.

10. A matrix sustained release device for the sustained release of fibroblast-derived growth factors which comprises:
   a. a biocompatible substrate of polymer beads having heparin or heparin sulfate bound thereto and the growth-factor-bound to the heparin or heparin sulfate; and
   b. a polymeric matrix acting as a supporting framework having a plurality of interconnecting channels which house the growth-factor-bound substrate.

* * * * *

UNITED STATES PATENT AND TRADEMARK OFFICE
CERTIFICATE OF CORRECTION

PATENT NO. : 5,100,668
DATED : March 31, 1992
INVENTOR(S) : Elazer R. Edelman, Robert S. Langer, Michael Klagsburn, Edith Mathiowitz It is certified that error appears in the above-identified patent and that said Letters Patent is hereby corrected as shown below:

Claim 1, column 8, line 4, should read as follows:

A device for controlling the release rate of a fibroblast derived growth factor which comprises a substrate of cross-linked dextran material having heparin or heparin sulfate bound thereto and the growth factor bound to the heparin or heparin sulfate.

Claim 8, column 8, line 23, cancel "polyactic" and insert therefor --polylactic--;

Claim 10, column 8, line 39, cancel "polymer beads" and insert therefor --cross-linked dextran beads--.

Signed and Sealed this

Fourteenth Day of September, 1993

BRUCE LEHMAN

*Attest:*

*Attesting Officer*    Commissioner of Patents and Trademarks